United States Patent
Kim et al.

[11] Patent Number: 5,952,461
[45] Date of Patent: Sep. 14, 1999

[54] PROCESS FOR PREPARING HUMAN PROINSULIN

[75] Inventors: Chang-Kyu Kim, Seoul; Yong-In Kim, Kyunggi-Do; Je-Nie Pheu, Kyunggi-Do; Jeong-Woo Shin, Kyunggi-Do; Sung-Jin Oh, Seoul, all of Rep. of Korea; Chung-Il Hong, New York, N.Y.; Jung-Woo Kim; Wang-Sik Lee, both of Seoul, Rep. of Korea

[73] Assignee: Chong Kun Dang Corporation, Seoul, Rep. of Korea

[21] Appl. No.: 09/009,145

[22] Filed: Jan. 20, 1998

[30] Foreign Application Priority Data

Dec. 29, 1997 [KR] Rep. of Korea .................. 97-77163

[51] Int. Cl.$^6$ .................................................. A61K 38/28
[52] U.S. Cl. .................... 530/305; 530/303; 530/304; 930/DIG. 620
[58] Field of Search .................... 530/303, 304, 530/305; 930/DIG. 620

[56] References Cited

U.S. PATENT DOCUMENTS

| | | | |
|---|---|---|---|
| 4,430,266 | 2/1984 | Frank | 530/303 |
| 4,451,396 | 5/1984 | Di Marchi | 530/402 |
| 4,616,078 | 10/1986 | DiMarchi | 530/305 |
| 4,801,684 | 1/1989 | Grau | 530/303 |
| 4,999,422 | 3/1991 | Galliher | 530/351 |
| 5,202,415 | 4/1993 | Jonassen et al. | 530/303 |
| 5,473,049 | 12/1995 | Obermeier et al. | 530/305 |

FOREIGN PATENT DOCUMENTS

| | | |
|---|---|---|
| 0055945 | 7/1982 | European Pat. Off. . |
| 0197764 | 10/1986 | European Pat. Off. . |
| 381958 | 1/1990 | European Pat. Off. . |

OTHER PUBLICATIONS

Guo et al., Shiyan Shengwu Xuebao, 25(2), "Genetic Engineering of Human Insulin—Purification and Characterization of Human Proinsulin and Insulin", pp. 157–163 in Chem. Abstr. (1993) vol. 118, Abstr. No. 20996, 1992.

Ki-Doo et al., Bull. Korean Chem. Soc., 18(8), "The Role of Highly Conserved Tetrapeptide Sequence of C-Peptide in the Folding of Proinsulin", pp. 798–800 in Chem. Abstr. (1997) vol. 127, Abstr. No. 272915,.

I.A. Mirsky et al., The Isolation and Crystallization of Human Insulin, J. Clin. Invest., 42:1869–1872 (1961).

W. Kemmler et al., Studies on the Conversion of Proinsulin to Insulin, J. Biol. Chem., 246:6786–6791 (1971).

J.S. Skyler et al., Symposium on Biosynthetic Human Insulin, Diabetes Care, 4:139–154 (1981).

E.P. Kroeff et al., Production Scale Purification of Biosynthetic Human Insulin by Reversed–Phase High–Performance Liquid Chromatography, J. Chromatogr., 461:45–61 (1989).

M.L.Brader and M.F. Dunn, Insulin Hexamers: New Conformations and Applications, Trends Biochem. Sci., 16:341–345 (1991).

B.Fischer et al., Isolation, Renaturation, and Formation of Disulfide et al., Isolation, Renaturation, and Formation of Disulfide Bonds of Eukaryotic Proteins Expressed in *Escherichia coli* as Inclusion Bodies, Biotechnol. Bioeng., 41;3–13 (1993).

M. Terashima et al., Effective Refolding of Fully Reduced Lysozyme with a Flow–Type Reactor, Process Biochem., 31:341–345 (1996).

A. Mukhopadhyay, Inclusion Bodies and Purification of Proteins in Biologically Active Forms, Advan. Biochem. Eng/Biotech., 56:62–109.

*Primary Examiner*—Jon P. Weber
*Attorney, Agent, or Firm*—Knobbe, Martens, Olson & Bear, LLP

[57] ABSTRACT

The present invention relates to a process for preparing human proinsulin which is represented as a following chemical formula(I):

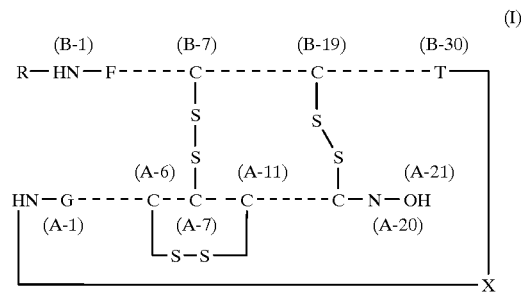

wherein, R is an amino acid residue or a peptide which is degradable enzymatically or chemically; and, X is a linkage of an amino group of A-1 in insulin A chain and a carboxyl group of B-30 in insulin B chain which can be separated from the A chain or the B chain enzymatically or chemically, provided that a region from A-1 to A-21 is the insulin A chain and a region from B-1 to B-30 is the insulin B chain. In accordance with the present invention, human recombinant insulin precursor can be simply manufactured with a good reproducibility, since dissolution, sulfonation, concentration, desalting and purification are remarkably simplified, while increasing the yield of refolding reaction.

17 Claims, 3 Drawing Sheets

PROCESS FOR PREPARING HUMAN PROINSULIN

FIELD OF THE INVENTION

The present invention relates to a process for preparing human proinsulin, more specifically, to a process for preparing human proinsulin which is represented as a following chemical formula (I):

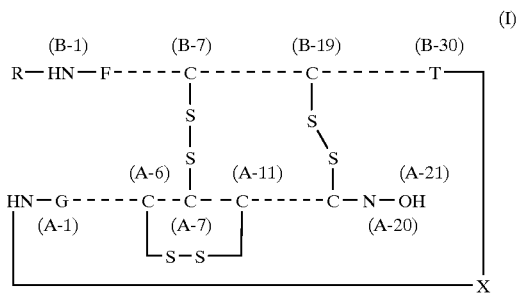

wherein,

R is an amino acid residue or a peptide which is degradable enzymatically or chemically; and X is a linkage of an amino group of A-1 in insulin A chain and a carboxyl group of B-30 in insulin B chain which can be separated from the A chain or the B chain enzymatically or chemically, provided that a region from A-1 to A-21 is the insulin A chain and a region from B-1 to B-30 is the insulin B chain.

BACKGROUND OF THE INVENTION

In general, human insulin precursor ("proinsulin") has been prepared in the course of manufacturing mature insulin ("insulin") by the recombinant DNA technology which comprises a step of inserting a structural gene into a plasmid DNA of E. coli.

As shown in FIG. 1, a fusion protein containing the proinsulin is expressed in the form of inclusion body in E. coli, and the inclusion bodies obtained by centrifugation after lysis of the cells are washed with non-ionic or ionic detergent, or with a denaturant at a low concentration. Such a treatment accompanied by centrifugation is repeated to result in increase of purity of the desired protein (see: Mukhopadhyay, A. et al., Advances in Biochemical Engineering/Biotechnology, 56, 61–108, 1997). In order to minimize intermolecular hydrophobic interaction and formation of incorrect disulfide bonds, the washed inclusion bodies are dissolved in a denaturant such as urea or guanidine.HCl solution containing a reducing agent such a dithiothreitol (DTT) or 2-mercaptoethanol, or in NaOH (see: Fischer et al., Biotechnology & Bioengineering, 41, 3–13, 1993). The dissolved inclusion bodies are centrifuged at a high speed, and the supernatant is diluted with cold water to recover the inclusion bodies as a precipitate (see: EP 0 055 945 A2). The inclusion bodies thus obtained contain a fusion protein of proinsulin and a heteroprotein such as β-galactosidase, which are linked by a cross-linkage of methionine residue. The fusion protein is treated with cyanogen bromide (CNBr), and substitution of six (6) —SH groups present in proinsulin with —SSO₃ groups follows to give proinsulin S-sulfonate. Such a sulfonation step leads to increase in stability of insulin precursor and efficiency of a later refolding reaction (see: EP 0 055 945 A2). The proinsulin S-sulfonate is refolded to have a native conformation by using reducing agents such as 2-mercaptoethanol, DTT, etc., or a redox system such as glutathione (see: Fischer et al., Biotechnology & Bioengineering, 43, 3–13, 1993). The native proinsulin thus obtained is converted into biologically active insulin by removing X (or C chain) which links A chain and B chain through the treatment of trypsin and carboxypeptidase B (see: Kemmler W., et al., J.B.C., 246, 6786–6790, 1971). Finally, insulin is purified through a reverse-phase high performance liquid chromatography (RP-HPLC), etc. (see: Kroeff, E. P., et al., J Chromatogr., 461, 45–61, 1989) and crystallized by the technique of Zn-crystallization (see: Mirsky, et al., J. Clinical Investigation, 42, 1869–1872, 1963; Brader, M. L., TIBS, 16, 341–345, 1991).

The conventional process for preparing proinsulin or insulin is, however, proven to be less satisfactory in the senses that: it accompanies complicated steps of dissolution and sulfonation, purification, concentration and desalting; and it employs an inefficient refolding reaction, which results in decreased yield of the desired protein. Accordingly, there are strong reasons for exploring and developing an improved process for preparing proinsulin or insulin in a simple and efficient manner, while preserving its biological activity.

SUMMARY OF THE INVENTION

The present inventors have made an effort to solve the problems of the conventional processes for preparing human recombinant proinsulin expressed in the form of inclusion body, and successfully established a process for preparing human proinsulin whose steps of dissolution and sulfonation, and purification, concentration and desalting are remarkably simplified, while increasing the efficiency of refolding reaction.

The primary object of the present invention is, therefore, to provide a simple process for preparing human recombinant proinsulin with a good reproducibility.

BRIEF DESCRIPTION OF THE DRAWINGS

The above and other objects and features of the present invention will become apparent from the following descriptions given in conjunction with the accompanying drawings, in which.

DETAILED DESCRIPTION OF THE PREFERRED EMBODIMENT

In accordance with the process for preparing human proinsulin of the present invention, human insulin precursor expressed in the form of inclusion body, is treated with sodium tetrathionate (Na₂S₄O₆) and sodium sulfite (Na₂SO₃) during a step of dissolution of the inclusion body in urea or guanidine.HCl solution, which results in substitution of —SH groups in cysteine residues of the insulin precursor with —SSO₃ groups, to give proinsulin S-sulfonate represented as the following chemical formula (II), which is converted into proinsulin represented as the chemical formula (I) by reacting the proinsulin S-sulfonate with 2-mercaptoethanol in an aqueous medium.

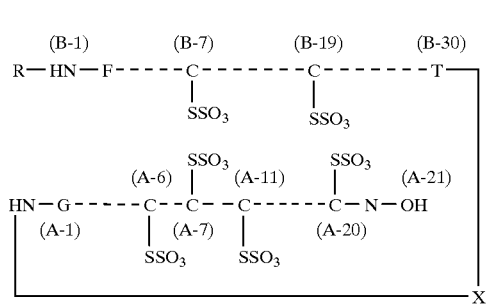

wherein,

R and X are the same as described above.

Figure 1:
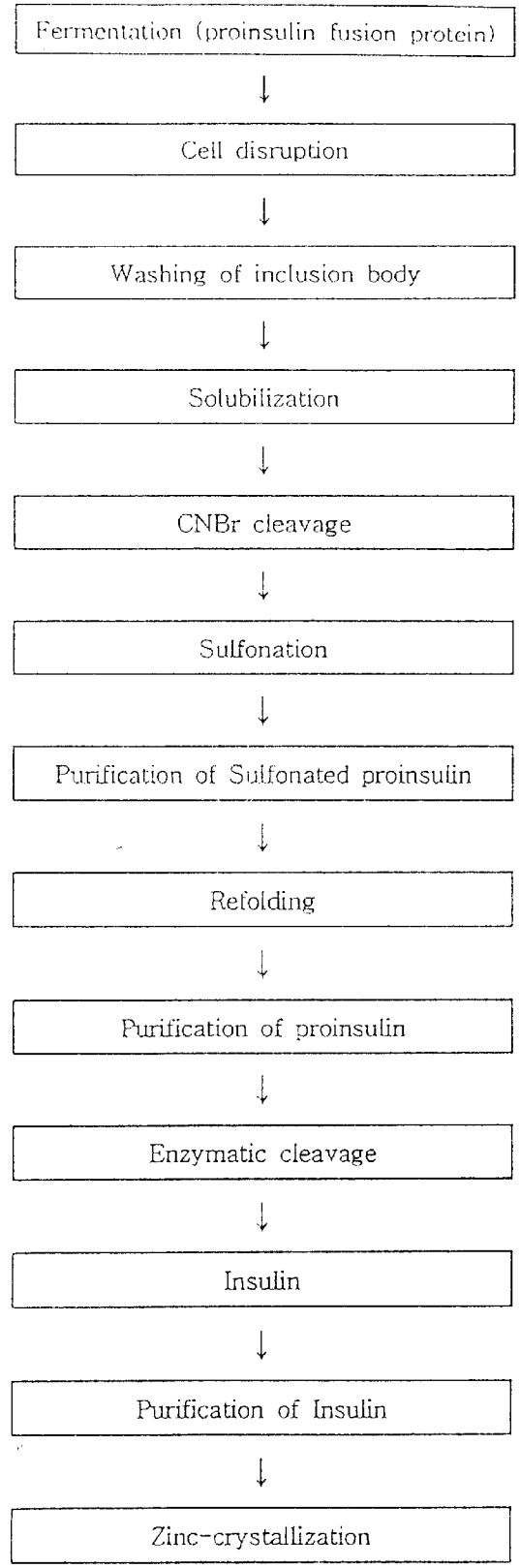
FIG. 1 is a schematic diagram showing a conventional process for preparing human insulin from a fused human insulin precursor which is expressed in recombinant E. coli.
Figure 2:
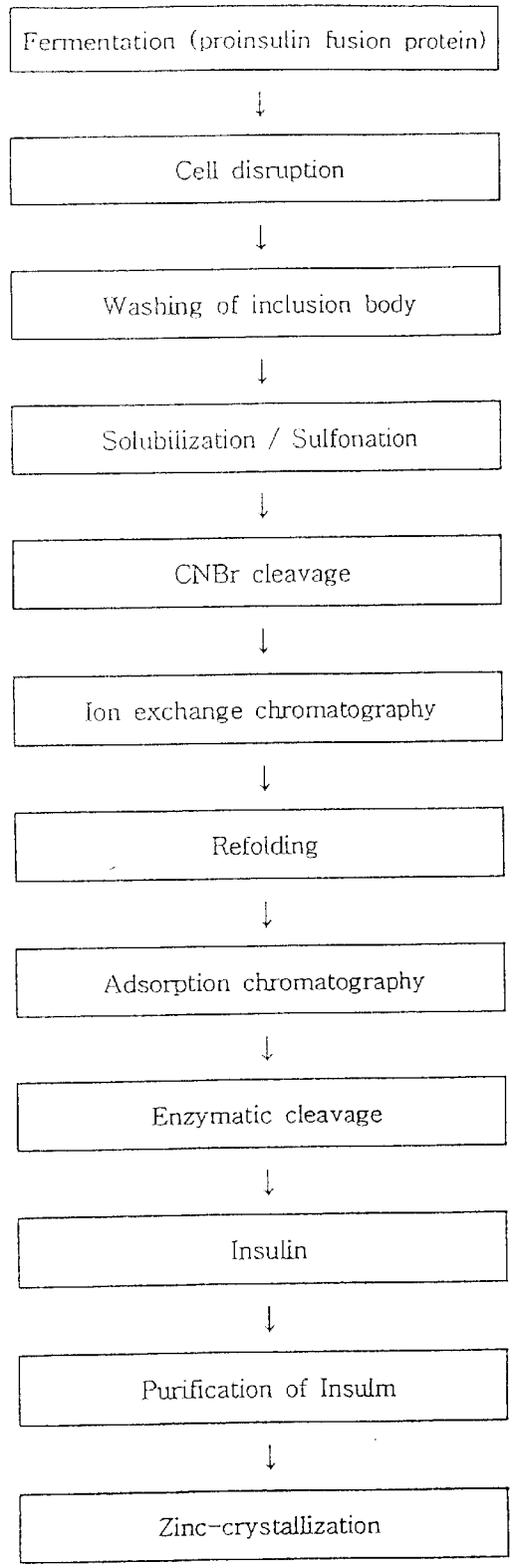
FIG. 2 is a schematic diagram showing a process for preparing human insulin from a fused human insulin precursor which is expressed in recombinant E. coli, in accordance with the present invention.
Figure 3:
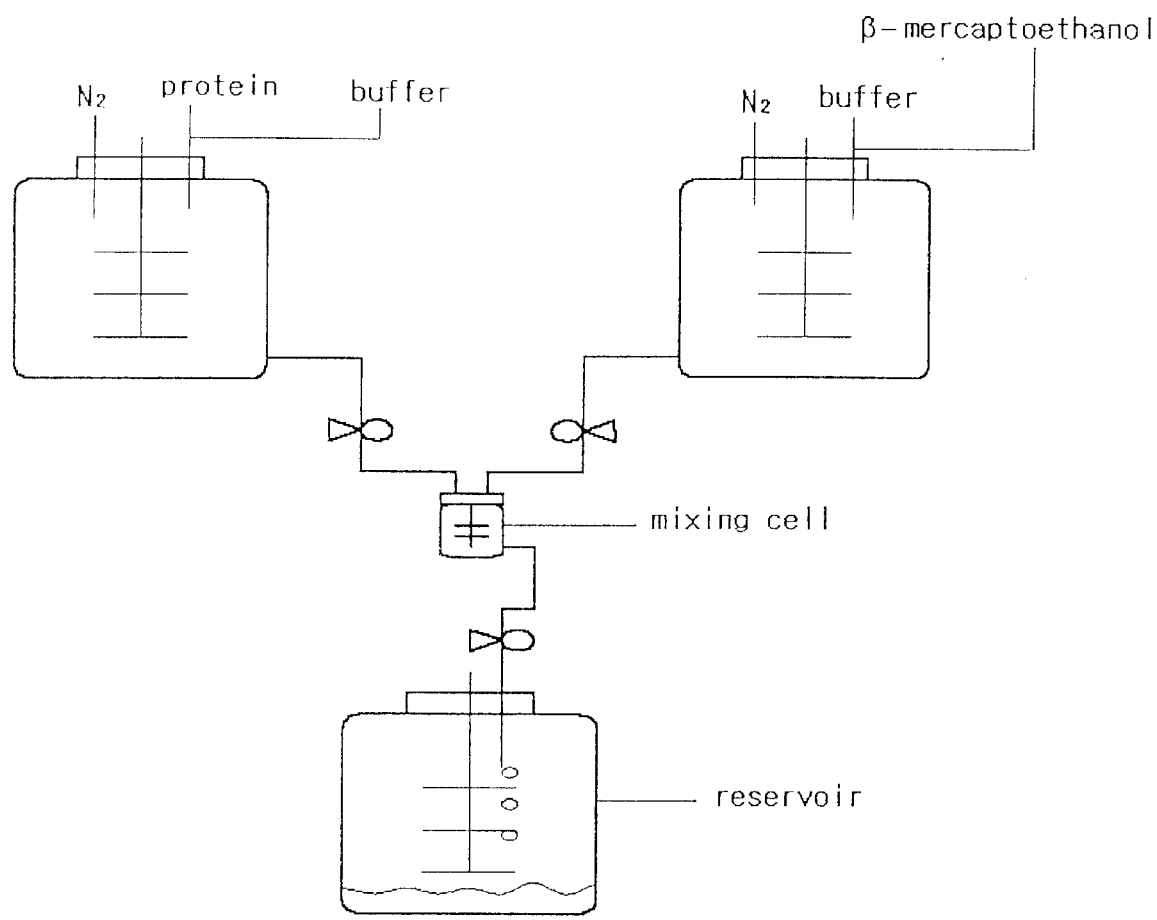
FIG. 3 depicts a refolding system employed in the process for preparing human proinsulin of the invention.

The process for preparing human proinsulin of the invention is described in more detail accompanied with FIGS. 2 and 3. In the process for preparing human proinsulin, all steps are preferably carried out at a low temperature of about 4° C., though they may be performed at a room temperature for the practitioner's convenience.

Step 1: Purification of inclusion bodies

In order to prepare a recombinant human insulin, the present inventors used a fusion protein of a modified β-galactosidase and proinsulin which is expressed in *E. coli* (see: Korean patent publication No. 94-1855). *E. coli* cells which express the fusion protein in the form of inclusion body are suspended in a buffer solution for lysis in a ratio of 1:5 to 10 (w/v), and lysed under a pressure of about 9,000 psi. The inclusion bodies are centrifuged and washed by using Triton X-100 and distilled water, and centrifuged to obtain purified inclusion bodies.

Step 2: Dissolution and sulfonation

The purified inclusion bodies are dissolved in 0.02M to 0.1M Tris buffer solution (pH 8 to 10) containing a denaturant of 6 to 8M urea or guanidine.HCl in a ratio of 1:10 to 20(w/v), more preferably 1:5 to 10(w/v), while adding 0.1 to 0.6M, more preferably 0.2 to 0.5M sodium sulfite ($Na_2SO_3$) and 0.01 to 0.1M, more preferably 0.05 to 0.1M sodium tetrathionate ($Na_2S_4O_4$). Then, the mixed solution containing the inclusion bodies are stirred to induce sulfonation of insulin precursor, which results in substitution of —SH groups of the insulin precursor with —$SO_3$ groups. In this step, pH and temperature are maintained in the ranges of pH 7.0–9.5 and 4° C.–8° C., respectively. Finally, sulfonated proinsulin fusion protein is obtained by substituting —SH groups in cysteine residues of the proinsulin with —$SO_3$ groups.

Step 3: Treatment with cyanogen bromide

After the sulfonation reaction, the reaction mixture is centrifuged at 12,000 rpm for 30 minutes to remove precipitates. Cold water is added to the supernatant in a ratio of 5 to 20:1(v/v), and pH is adjusted to 5 to 6 to give a precipitate. The precipitated protein is dissolved in 70% (v/v) formic acid to reach a concentration of 10–30 mg/ml, and is subsequently treated with cyanogen bromide so that the molar ratio of the cyanogen bromide to protein is 100:1. This results in separation of the proinsulin S-sulfonate from the fusion protein. And then, drying is carried out under a reduced pressure.

Step 4: Ion-exchange chromatography

Proinsulin S-sulfonate is dissolved in 20 mM Tris buffer (pH 8.0) containing 1 mM EDTA and 7M urea to reach a concentration of 30 mg/ml and loaded onto a DEAE-Sephacel resin equilibrated with the same buffer. Then, elution is made by employing a concentration gradient of 0–1M NaCl, to give the proinsulin S-sulfonate in the concentration range of 0.3–0.5M NaCl.

Step 5: Refolding (Conversion of proinsulin S-sulfonate to proinsulin)

The purified proinsulin S-sulfonate is diluted with 50 mM glycine buffer (pH 10.6) containing 1M urea in a concentration of 1–10 mg/ml, without desalting or pretreatment. Then, nitrogen gas is purged to remove oxygen and the chamber is sealed well. In another chamber, 2-mercaptoethanol is added to 50 mM glycine buffer (pH 10.6) containing 1M urea in an equivalent ratio of 1 to 3 against —$SO_3$ groups of proinsulin S-sulfonate. And then, the protein solution and the buffer solution containing 2-mercaptoethanol are mixed rapidly in a ratio of 1:1(v/) by connecting the two chambers to a mixing cell, and the refolding reaction mixture is introduced into a reservoir while stirring slowly and reacted for 15 to 20 hours at 4–5° C. (see: FIG. 3). By carrying out the refolding step, at least 80% of proinsulin S-sulfonate can be converted into native proinsulin.

Step 6: Adsorption chromatography

The refolding reaction mixture containing the refolded proinsulin is contacted with a polar methacrylate resin of HP-2MG, while adjusting the reaction mixture in a pH range of 3 to 4, so that 8 g of the mixed proteins containing the refolded proinsulin can contact with 1 liter of the resin. In this connection, the refolding reaction is stopped by adjusting pH to acidic range, and protein concentration of the loading sample is controlled in a range of 0.1 mg/ml to 5 mg/ml, depending on the condition of the proinsulin refolding reaction. After adsorption, the resin is washed with acetic acid buffer (pH 3 to 4), and desalting and concentration of the refolded insulin precursor is made by the elution using an aqueous eluent of acetic acid buffer (pH 3 to 4) containing 15% to 50%, preferably 30% to 50% of acetone.

The process for preparing a human insulin precursor of the invention has following advantages over the conventional processes: first, dissolution and sulfonation are carried out simultaneously, which results in simplification of steps for production; secondly, denaturation such as gelation occurring by intermolecular polymerization in a sample of high concentration can be successfully prevented; thirdly, the problem of decrease in solubility of a sample caused by incorrect homogenous mixing of reactants such as proinsulin S-sulfonate and 2-mercaptoethanol is not performed rapidly, which can lead to the aggregation to decrease refolding yield, since a large reaction volume is required for the refolding reaction of insulin on industrial scale. Under the circumstances, in order to reduce the time required for equilibrium during mixing of proinsulin S-sulfonate and 2-mercaptoethanol, the present inventors have carried out a refolding reaction by mixing them continuously in a mixing cell of a small volume, which finally provides proinsulin in a high yield, even though a highly concentrated proinsulin S-sulfonate is employed.

In order to purify the refolded proinsulin after the refolding reaction, gel filtration chromatography such as Sephadex G-50 and ion-exchange chromatography are generally employed, which essentially require a step of changing of buffer solution and a step of desalting to remove remaining salts (see: U.S. Pat. No. 4,430,266). The conventional desalting methods include gel filtration, dialysis, ultrafiltration, etc. Among them, gel filtration employs polydextran gel such as Sephadex G-25 to separate substances depending on molecular weight or structure of the substances, based on the difference in retention time for the substances to pass through the gel. On the other hand, a dialysis membrane, instead of the gel, is used for dialysis technique, and a cartridge such as hollow fiber and cassette, and a disc membrane are used for ultrafiltration.

However, the said methods have revealed the following several shortcomings: That is, carrying out the gel filtration, sample capacity depends on gel volume packed in a column rather than quantity or concentration of the sample (capacity: 10% to 25% of gel volume). Thus, if a large column is employed in the gel filtration, the applied sample should be diluted, which gives troubles in the later steps. Also, the eluted sample is diluted, which gives troubles in the later steps. On the other hand, the dialysis technique has drawbacks of sample loss caused by nonspecific binding of the sample to the dialysis membrane and the limited capacity as well. Ultrafiltration has also disadvantages of requirement of a specific equipment, sample loss caused by nonspecific binding, fouling and plugging, and decrease in flow rate, although it has advantages of high capacity and efficient concentration capability.

In accordance with the present invention, a step of desalting, unlike the conventional processes, is performed employing adsorption chromatography, which successfully solves the said problems, i.e., limited capacity, dilution of the sample, nonselective binding, etc. Practically, a refolding reaction solution containing active proinsulin is adjusted to an acidic condition of pH 3 to 4; and loaded onto a polar methacrylate resin to recover almost all active proinsulin by using a buffer solution(pH 3 -to 4) containing 15% to 50% acetone. In this connection, the polar methacrylate resin under a trademark of HP-2MG which is commercially available from Mitsubishi Chemical Co. is employed for the adsorption of organic substances showing relatively high polarity. The adsorption/elution step is carried out in a column for the best efficiency of desalting, concentration and purification. However, it may be performed in a way of batch or column. In this step, more than 90% of yield, and efficient concentration of several to dozens times can be accomplished, depending on the concentration of the loading sample.

In short, the refolded proinsulin can be economically desalted, concentrated, and purified in one step, and the element itself can be directly used in later steps.

The present invention is further illustrated in the following examples, which should not be taken to limit the scope of the invention.

EXAMPLE 1

Purification of Inclusion Bodies

E. coli cells which express proinsulin fusion proteins in a form of inclusion body (see: Korean patent publication No. 94-1855) were suspended in 0.1 M Tris buffer (pH 7.9) containing 50 mM EDTA, 1096 sucrose and 0.1 mM PMSF in a ratio of 1:5 to 10 (w/v) and lysed under a pressure of 9,000 psi. The lysate was centrifuged at 5,000 rpm for 30 minutes at 4° C. to obtain precipitate. 300 g (wet weight) of the precipitate containing inclusion bodies was washed with 10 volume of 2% Triton-X100 and distilled water, and centrifuged to obtain purified inclusion bodies.

EXAMPLE 2

Dissolution of Inclusion Bodies by Alkali

The inclusion bodies obtained in Example 1 were suspended uniformly in 20 volumes of distilled water, stirred for 3 hours, and centrifuged at 12,000 rpm for 30 minutes to remove precipitate. The pH of the supernatant thus obtained was adjusted to 5.5 with 1M HCl and centrifuged at 5,000 rpm for 30 minutes to obtain precipitate. The precipitated protein was dissolved in 70% (v/v) formic acid to reach a concentration of 10 mg/ml. Then, cyanogen bromide was added in a molar ratio of 100:1 against the amount of the protein, and stirred for 12 hours at 25° C. And then, evaporation was Tris buffer (pH 9.5) containing 7M urea. Sodium sulfite and sodium tetrathionate were added in a final concentration of 0.3M and 0.1M, respectively, and stirred for 6 hours. And then, HPLC analysis was carried out to determine concentration of the sulfonated proinsulin(see: Table 1).

EXAMPLE 3

Dissolution of Inclusion Bodies by Guanidine.HCL and Reducing Agents

The inclusion bodies obtained in Example 1 were suspended in 10 volume of several buffer solutions containing a denaturant as followings: first, they were dissolved in 20 mM Tris buffer (pH 9.5) containing 6–7M guanidine.HCl and 1 mM EDTA; secondly, they were dissolved in 20 mM Tris buffer-(pH 9.5) containing 6–7M guanidine.HCl and 1 mM EDTA, and 1 mM 2-mercaptoethanol was added; thirdly, they were dissolved in 20 mM Tris buffer (pH 9.5) containing 6–7M guanidine.HCl and 1 mM EDTA, and sodium sulfite and sodium tetrathionate were added in a final concentration of 0.3M and 0.1M, respectively. And then, each solution was stirred for 12 hours at 4° C., and centrifuged at 12,000 rpm for 30 minutes to remove precipitate. Then, about 10 volume of cold water was added to the supernatant thus obtained and centrifuged at 5,000 rpm for 30 minutes to obtain precipitate. The precipitated protein was dissolved in 70%(v/v) formic acid to reach a concentration of 10 mg/ml. Then, cyanogen bromide was added in a molar ratio of 100:1 against the amount of the protein, and stirred for 12 hours at 25° C. And then, evaporation was carried out for complete drying and the protein thus obtained was dissolved in 20 mM Tris buffer (pH 9.5) containing 7M urea/Sodium sulfite and sodium tetrathionate were added in a final concentration of 0.3M and 0.1M, respectively, and stirred for 6 hours at 25° C. And then, HPLC analysis was carried out to determine concentration of the sulfonated proinsulin (see: Table 1).

EXAMPLE 4

Dissolution of Inclusion Bodies by Urea and Reducing Agents

The inclusion bodies obtained in Example 1 were suspended in 10 volume of several buffer solutions containing a denaturant as followings: first, they were dissolved in 20 mM Tris buffer (pH 9.5) containing 7–8M urea and 1 mM EDTA; secondly, they were dissolved in 20 mM Tris buffer(pH 9.5) containing 7–8M urea and 1 mM EDTA, and 1 mM 2-mercaptoethanol was added; thirdly, they were dissolved in 20 mM Tris buffer(pH 9.5) containing 7–8M urea and 1 mM EDTA, and sodium sulfite and sodium tetrathionate were added in a final concentration of 0.3M and 0.1M, respectively, And then, each solution was stirred for 12 hours at 4° C., and centrifuged at 12,000 rpm for 30 minutes to remove precipitate. Then, about 10 volume of cold water was added to the supernatant thus obtained and centrifuged at 5,000 rpm for 30 minutes to obtain precipitate. The precipitated protein was dissolved in 70% (v/v)

formic acid 5 to reach a concentration of 10 mg/ml. Then, cyanogen bromide was added in a molar ration of 100:1 against the amount of the protein, and stirred for 12 hours at 25° C. And then, evaporation was carried out for complete drying and the protein thus obtained was sulfite and sodium tetrathionate were added in a final concentration of 0.3M and 0.1M, respectively, and stirred for 6 hours at 25° C. And then, HPLC analysis was carried out to determine concentration of the sulfonated proinsulin (see: Table 1).

TABLE 1

Effect of various dissolving methods in Examples 2 to 4 on sulfonation [1]

| Treatment | Amount of protein after dissolution (g) | Yield of sulfonation (%) (sulfonated proinsulin g/amount of protein) |
|---|---|---|
| Control | 10.2 | 28.6 |
| Dissolution by alkali | 7 | 6.7 |
| Dissolution by HCl.guanidine | — | — |
| Dissolution by HCl.guanidine + 1 mM 2-mercaptoethanol | 7.1 | 24 |
| Dissolution by HCl.guanidine + sulfite + tetrathionate | 6.3 | 48 |
| Dissolution by urea | 7.0 | 31.5 |
| Dissolution by urea + 1 mM 2-mercaptoethanol | 7.1 | 28 |
| Dissolution by urea + sulfite + tetrathionate | 6.2 | 45.2 |

[1] Each sample employed 30 g (in wet weight) of inclusion bodies washed with Triton X-100 and cold distilled water, and the same amount of inclusion bodies treated with CNBr only, is employed as control.

As can be seen in Table 1, addition of sodium sulfite and sodium tetrathionate after dissolution by urea or guanidine. HCL resulted in an increased yield of sulfonated proinsulin, which is 1.5 to 2 times as high as than the control. On the other hand, when dissolution was carried out by only guanidine.HCL without any reducing agent, gelation occurred in the course of adding 70%(v/v) formic acid. Therefore, the amount of protein after dissolution and yield of sulfonation could not be determined. Such a result may be caused by intermolecular hydrophobic interaction or polymerization by formation of disulfide bond. Also, addition of 2-mercaptoethanol resulted in a considerable decrease in yield, which may also be caused by the same reasons described above.

It was clearly demonstrated that: the intermolecular interaction can be prevented through the substitution with $—SSO^-_3$ groups in sulfonated proinsulin fusion protein to give negative charge to the whole molecule; and, dissolution by alkali influences stability of the proteins. On the other hand, addition of sulfite and tetrathionate after dissolution by urea or guanidine.HCL, has no remarkable difference in the yield of sulfonated proinsulin. Therefore, use of urea for dissolution on industrial scale would result in a remarkable reduction in cost.

In addition, HPLC analysis of the sample which was obtained through the steps of dissolution and sulfonation, cyanogen bromide treatment and dissolution in 20 mM Tris buffer containing 7M urea, has revealed that: the sulfonated proinsulins were obtained in an equal amount, even though sulfite and tetrathionate.

EXAMPLE 5

Dissolution of Inclusion Bodies by Urea and Sulfonation

Based on the results in Example 2 to 4 described above, the inclusion bodies were dissolved in a urea solution and sulfonation was carried out. That is, 110 g (in wet weight) of the purified inclusion bodies were dissolved in 10 volume of 20 mM Tris buffer (pH 8.5) containing 8M urea and 1 mM EDTA. Then, sodium sulfite and sodium tetrathionate were added in a final concentration of 0.3M and 0.1M, respectively, stirred for 12 hours at 4° C., and centrifuged at 12,000 rpm for 30 minutes to remove precipitate. And then, about 10 volume of cold water was added to the supernatant thus obtained, and pH of the solution was adjusted to about 5.5 with 2N HCl solution, and centrifuged at 5,000 rpm for 30 minutes to give precipitate of 250 g in wet weight. Quantitative assay of protein revealed that about 40 g of protein was finally obtained.

EXAMPLE 6

Treatment with Cyanogen Bromide

The precipitated protein was dissolved in 2 L of 70% (v/v) formic acid. Then, cyanogen bromide (CNBr) was added in a molar ration of 100:1 against the amount of the protein, and stirred for 12 hours at 25° C. And then, evaporation was carried out for complete drying. The protein thus obtained was dissolved in 20 mM Tris buffer (pH 8.0) containing 7M urea, and analyzed by HPLC.

EXAMPLE 7

Anion-exchange Chromatography

DEAE-Sephacel was packed in a column (2.5×30 cm) at a flow rate of 1.5 column volume per hour, and equilibrated with 20 mM Tris buffer(pH 8.0) containing 7M urea. Then, the sample obtained in Example 6 was loaded onto the column at a rate of 20 mg per 1 ml of the resin, and the column was washed with 1 column volume of the equilibrium buffer. The protein was eluted by a concentration gradient by using the equilibrium buffer containing 0–1M NaCl. Then, the eluents collected at 0.35–0.45M NaCl were analyzed by HPLC, which revealed that purity was 80% or more and recovery rate was 91%.

EXAMPLE 8

Refolding of Proinsulin S-sulfonate 1 g of proinsulin S-sulfonate which was obtained by sulfonating recombinant proinsulin purified by RP-HPLC, was dissolved in 500 ml of 50 mM glycine buffer (pH 10.6). Then, nitrogen gas was purged to remove oxygen and the chamber was sealed well. In another chamber, 104 $\mu$l of 2-mercaptoethanol was added to 500 ml of 50 mM glycine buffer (pH 10.6), nitrogen gas was also purged to remove oxygen and the chamber was sealed well. And then, the two solutions were rapidly introduced into a mixing cell having a volume of 1 ml at a flow rate of 50 ml/hr while stirring. The refolding reaction solution thus mixed was introduced into a reservoir purged with $N_2$ gas at a flow rate of 100 ml/hr, stirred slowly, and reacted for 18 hours at 4° C. After the reaction was completed, the solution was acidified to give pH 2.9±0.1 by using 2M HCl. HPLC analysis revealed that refolding yield was 55%.

EXAMPLE 9

Effect of Protein Concentration on Refolding

Effect of protein concentration on the yield of refolding (i.e., conversion of proinsulin S-sulfonate to proinsulin) was investigated, through a series of reactions performed analogously as in Example 8 except for the protein concentration (see: Table 2).

TABLE 2

Effect of protein concentration on the yield of refolding

| Protein concentration (mg/ml) | Yield (%) | Protein concentration (mg/ml) | Yield (1%) |
|---|---|---|---|
| 0.1 | 95 | 1 | 53 |
| 0.2 | 90 | 2 | 20 |
| 0.5 | 83 | 4 | 8 |

EXAMPLE 10

Effect of —SH:—SSO$^-_3$ Ratio on Refolding

Effect of —SH:—SSO$^-_3$ ratio on the yield of refolding was investigated through a series of reactions performed analogously as in Example 8 except for the —SH:—SSO$^-_3$ ratio (see: Table 3).

TABLE 3

Effect of -SH:-SSO$_3$ ratio on the yield of refolding

| -SH:-SSO$_3$- ratio | Yield (%) | -SH:-SSO$_3$- ratio | Yield (%) |
|---|---|---|---|
| 1 | 41 | 2 | 54 |
| 1.5 | 59 | 3 | 30 |

EXAMPLE 11

Effect of Urea Concentration on Refolding

Effect of urea concentration on the yield of refolding was investigated through a series of reactions performed analogously as in Example 8 except for urea concentrations (see: Table 4).

TABLE 4

Effect of urea concentration on the yield of refolding

| Urea concentration (M) | Yield (%) | Urea concentration (M) | Yield (%) |
|---|---|---|---|
| 0 | 52 | 0.5 | 79 |
| 0.25 | 67 | 1.0 | 83 |

EXAMPLE 12

Refolding of Proinsulin S-sulfonate Purified by Ion-exchange Chromatography

Eluent containing log of proinsulin S-sulfonate obtained in Example 7 was diluted with 50 mM glycine buffer (pH 10.6) containing 1M urea to reach a final volume of 5 L. Then, nitrogen gas was purged to remove oxygen and the chamber was sealed well. In another chamber, 781 µl of 2-mercaptoethanol was added to 5 L of 50 mM glycine buffer containing 1M urea, nitrogen gas was purged to remove oxygen and the chamber was sealed well. And then, the two solutions were mixed rapidly, by introducing into a mixing cell having a volume of 1 ml at a flow rate of 500 ml/hr while stirring. The refolding reaction mixture was introduced into a reservoir purged with N$_2$ gas at a flow rate of 1 L/hr, stirred slowly, and reacted for 18 hours at 4° C. After the reaction was completed, the solution was acidified to give pH 2.9±0.1 by using 2M HCl. HPLC analysis revealed that refolding yield was 81%.

EXAMPLE 13

Purification of Human Recombinant Proinsulin by Adsorption Chromatography

HP-2MG resin (Mitsubishi Chemical Co., Japan), a polar methacrylate resin, was swollen in a ratio of 1 g of a resin per 5 ml of acetone for 6 hours at room temperature. Then, the resin was sufficiently washed with 0.1N NaOH, distilled water, 0.1N HCl, distilled water and 20 mM acetic acid(pH 3.2±0.2) in order, and packed in a column, And then, the column was equilibrated with 3 column volume of an equilibrium buffer (20 mM acetic acid, pH 3.2±0.2) at a flow rate of 1 column volume per hour. Then, the reaction solution containing refolded proinsulin obtained in Example 12 was loaded onto the column in a ratio of 8 g of the protein per 1 L of the resin, and the column was washed with 1 column volume of 20 mM acetic acid buffer (pH 3.2±0.2). And then, active proinsulin was eluted with the same buffer containing 30% acetone. As a result, 92% or more of the refolded proinsulin was recovered, while being free from impurities such as glycine and urea. Also, HPLC and quantitative protein assay revealed that protein was concentrated in about 10-fold with an increased purity of about 1.3-fold. Then, the said eluent containing refolded proinsulin was evaporated to remove acetone and freeze-dried, or pH of the eluent was adjusted to 5.4 with 1N NaOH and zinc chloride was added in a final concentration of 0.04%(w/v) to recover the refolded proinsulin.

As clearly illustrated and demonstrated as above, the present invention provides a process for preparing human proinsulin whose steps of dissolution, sulfonation, concentration, desalting and purification are remarkably simplified while increasing the yield of refolding reaction. In accordance with the present invention, human recombinant insulin precursor can be simply manufactured with a good reproducibility.

What is claimed is:

1. A process for preparing human proinsulin which comprises the steps of:

(i) suspending in a buffer solution E. coli cells which express proinsulin fusion proteins in the form of an inclusion body and lysing said cells to obtain the inclusion body;

(ii) suspending said inclusion body obtained in step (i) in a buffer solution containing a denaturant, while sulfonating the proinsulin fusion proteins with sodium sulfate and sodium tetrathionate, to obtain fusion protein of proinsulin S-sulfonate represented as the following formula (II), Formula(II)

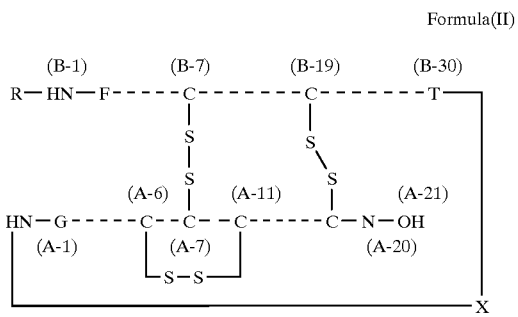

wherein,
R is an amino acid residue or a peptide which is degradable enzymatically or chemically; and
X is a linkage of an amino group of A-1 in insulin A chain and a carboxyl group of B-30 in insulin B chain which can be separated from the A chain or the B chain enzymatically or chemically, provided that a region from A-1 to A-21 is the insulin A chain and a region from B-1 to B-30 is the insulin B chain;
(iii) centrifuging the fusion protein of proinsulin S-sulfonate obtained in step (ii) to produce a precipitate, dissolving the precipitate in formic acid, then cleaving proinsulin S-sulfonate from said fusion protein by treating with cyanogen bromide and drying under a reduced pressure;
(iv) dissolving the dried proinsulin S-sulfonate obtained in step (iii) in a buffer and purifying said proinsulin S-sulfonate on anion-exchange chromatography;
(v) diluting said purified proinsulin S-sulfonate obtained in step (iv) in a first buffer solution, purging nitrogen gas to remove oxygen to obtain a first mixture, mixing the first mixture with a second buffer solution containing 2-mercaptoethanol, and stirring in a reservoir to obtain a refolding reaction mixture containing proinsulin represented as the following formula (I), Formula(I)

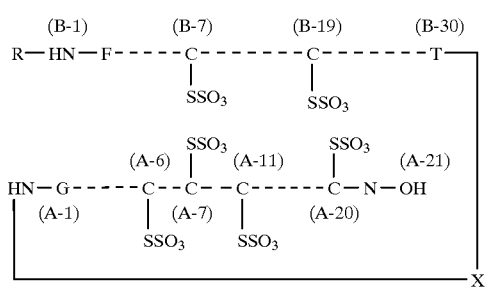

wherein, R and X are as defined above in connection with Formula (II); and
(vi) applying the refolding reaction mixture contained in step (v) to an adsorption chromatography resin and eluting by an aqueous solution, to give refolded human proinsulin.

2. The process for preparing human proinsulin of claim 1, wherein the denaturant is urea or guanidine.HCl.

3. The process for preparing human proinsulin of claim 1, wherein the concentration of the denaturant ranges from 6 to 8M.

4. The process for preparing human proinsulin of claim 1, wherein the inclusion body is suspended in 0.02 M to 0.1M Tris buffer solution (pH 8 to 10) containing the denaturant.

5. The process for preparing human proinsulin of claim 1, wherein the concentrations of sodium sulfite and sodium tetrathionate range from 0.1 to 0.6M and from 0.01 to 0.1 M, respectively.

6. The process for preparing human proinsulin of claim 1, wherein the inclusion body is suspended in the buffer solution containing the denaturant in a ratio of 10 to 20 (w/v).

7. The process for preparing human proinsulin of claim 1, wherein the inclusion body is suspended in the buffer solution containing the denaturant at a reaction temperature of 4° C. to 8° C.

8. The process for preparing human proinsulin of claim 1, wherein the dried proinsulin S-sulfonate is dissolved in Tris buffer (pH 7 to 9) containing 1 mM EDTA and 7M urea and purified on anion-exchange chromatography equilibrated with the same buffer.

9. The process for preparing human proinsulin of claim 1, wherein the purified proinsulin S-sulfonate is diluted with a glycine buffer solution (pH 9 to 11) containing 1M urea in a concentration of 0.1 to 10 mg/ml.

10. The process for preparing human proinsulin of claim 1, wherein 2-mercaptoethanol is added to a buffer solution containing 1M urea in an equivalent ratio of 1 to 3 with respect to the —$SSO_3$ groups of proinsulin S-sulfonate.

11. The process for preparing human proinsulin of claim 1, wherein the buffer solution containing diluted proinsulin S-sulfonate and the buffer solution containing 2-mercaptoethanol are mixed in a ratio of 1:1(v/v).

12. The process for preparing human proinsulin of claims 10 or 11, wherein the buffer solution employed is 50 mM glycine buffer solution(pH 10.6).

13. The process for preparing human proinsulin of claim 11, wherein the mixing is carried out in a mixing cell having a volume of 0.1 ml to 100 ml.

14. The process for preparing human proinsulin of claim 1, wherein the adsorption chromatography employs a polar methacrylate resin sold under the trademark of HP-2MG.

15. The process for preparing human proinsulin of claim 14, wherein the refolding reaction mixture is adsorbed to the polar methacrylate resin at a pH value of 3 to 4.

16. The process for preparing human proinsulin of claim 14, wherein the polar methacrylate resin is washed with acetic acid buffer (pH 3 to 4) before the elution of the refolded human proinsulin is made.

17. The process for preparing human proinsulin of claim 1, wherein the aqueous solution is acetic acid buffer solution (pH 3 to 4) containing 15% to 50% acetone.

* * * * *

UNITED STATES PATENT AND TRADEMARK OFFICE
CERTIFICATE OF CORRECTION

PATENT NO.   : 5,952,461
DATED        : September 14, 1999
INVENTOR(S)  : Kim et al.

It is certified that error appears in the above-identified patent and that said Letters Patent is hereby corrected as shown below:

Title page,
Item [12], below "United States Patent", replace "Kim et al." with -- Hong et al. --
Item [75], Inventors, please move "Chung-Il Hong, New York, N.Y.;" so that this name appears first amongst eight inventors listed.

Column 4,
Line 16, please replace "(v/)" with -- (v/v) --.

Column 5,
Line 55, please replace "1096" with -- 10% --.

Column 6,
Line 9, between "was" and "Tris", please insert -- carried out for complete drying and the protein thus obtained was dissolved in 20mM --.
Line 42, please replace "urea/Sodium" with -- urea. Sodium --.

Column 7,
Line 1, please delete "5".
Line 5, between "was" and "sulfite", please insert -- dissolved in 20mM Tris buffer (pH 9.5) containing 7M urea. Sodium --.
Line 61, after "tetrathionate", please insert -- were not added --.

Column 9,
Line 55, please replace "log" with -- 10g --.

Column 10,
Line 65, please replace "sulfate" with -- sulfite --.
Line 4-13, please replace the chemical formula with the following chemical formual:

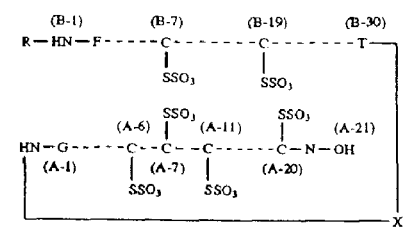

UNITED STATES PATENT AND TRADEMARK OFFICE
CERTIFICATE OF CORRECTION

PATENT NO.    : 5,952,461
DATED         : September 14, 1999
INVENTOR(S)   : Kim et al.

It is certified that error appears in the above-identified patent and that said Letters Patent is hereby corrected as shown below:

Column 10 (cont'd),
Lines 43-53, please replace the chemical formula with the following chemical formula:

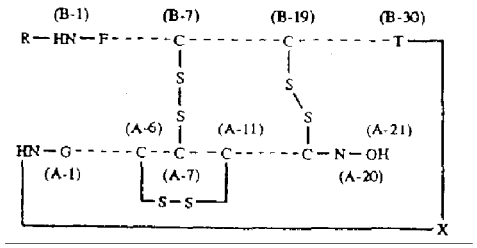

Signed and Sealed this

Thirteenth Day of July, 2004

JON W. DUDAS
*Acting Director of the United States Patent and Trademark Office*